(12) United States Patent
Park et al.

(10) Patent No.: US 8,852,111 B2
(45) Date of Patent: Oct. 7, 2014

(54) ULTRASOUND GUIDANCE SYSTEM

(75) Inventors: Robert Park, Durham, NC (US); Colin Kelemen, Wilmington, NC (US); Paul Nuschke, Durham, NC (US); Theodore J. Mosler, Raleigh, NC (US); Scott P. Jarnagin, Raleigh, NC (US); Todd M. Korogi, Raleigh, NC (US); Bryan J. Peters, Raleigh, NC (US)

(73) Assignee: Ultrasound Ventures, LLC, Durham, NC (US)

( * ) Notice: Subject to any disclaimer, the term of this patent is extended or adjusted under 35 U.S.C. 154(b) by 1418 days.

(21) Appl. No.: 11/508,300

(22) Filed: Aug. 23, 2006

(65) Prior Publication Data

US 2007/0073155 A1  Mar. 29, 2007

Related U.S. Application Data

(60) Provisional application No. 60/808,552, filed on May 26, 2006, provisional application No. 60/714,192, filed on Sep. 2, 2005.

(51) Int. Cl.
| | | |
|---|---|---|
| *A61B 8/00* | (2006.01) | |
| *A61B 17/34* | (2006.01) | |
| *A61B 8/08* | (2006.01) | |
| *A61B 19/08* | (2006.01) | |

(52) U.S. Cl.
CPC ........... *A61B 8/4218* (2013.01); *A61B 17/3403* (2013.01); *A61B 8/4472* (2013.01); *A61B 8/4455* (2013.01); *A61B 19/081* (2013.01); *A61B 2017/3413* (2013.01); *A61B 8/0833* (2013.01); *A61B 8/0841* (2013.01)

USPC ............ 600/461; 600/407; 600/437; 600/459

(58) Field of Classification Search
USPC .................................. 600/461, 407, 437, 459
See application file for complete search history.

(56) References Cited

U.S. PATENT DOCUMENTS

| | | | | |
|---|---|---|---|---|
| 4,058,001 | A | * | 11/1977 | Waxman ........................ 600/443 |
| 4,058,114 | A | * | 11/1977 | Soldner ......................... 600/461 |
| 4,346,717 | A | | 8/1982 | Haerten |
| 4,567,896 | A | | 2/1986 | Barnea |
| 4,576,175 | A | * | 3/1986 | Epstein ......................... 600/461 |
| 4,899,756 | A | | 2/1990 | Somek |
| 5,095,910 | A | | 3/1992 | Powers |
| 5,100,387 | A | | 3/1992 | Ng |

(Continued)

FOREIGN PATENT DOCUMENTS

| | | |
|---|---|---|
| EP | 1 552 792 A1 | 7/2005 |
| JP | 63-059610 | 4/1988 |

(Continued)

OTHER PUBLICATIONS

International Search Report for PCT/US06/33145, mailed Dec. 21, 2007, 9 pgs.

(Continued)

*Primary Examiner* — Peter Luong

(57) ABSTRACT

A compact ultrasound needle guidance system and method of use is described. The needle guidance system has components to adjustably target a needle's destination in the plane of a two-dimensional ultrasound image before insertion of a needle into a patient. Needle movement is tracked using a position detector that provides a visual display of the needle path on the ultrasonic image.

1 Claim, 15 Drawing Sheets

(56) References Cited

U.S. PATENT DOCUMENTS

| | | | |
|---|---|---|---|
| 5,280,427 A * | 1/1994 | Magnusson et al. | 600/407 |
| 5,479,927 A * | 1/1996 | Shmulewitz | 600/445 |
| 5,647,373 A | 7/1997 | Paltieli | |
| 5,660,185 A | 8/1997 | Shmulewitz et al. | |
| 5,924,992 A | 7/1999 | Park et al. | |
| 6,216,029 B1 | 4/2001 | Paltieli | |
| 6,296,614 B1 | 10/2001 | Pruter | |
| 6,361,499 B1 * | 3/2002 | Bates et al. | 600/461 |
| 6,379,307 B1 | 4/2002 | Filly et al. | |
| 6,689,067 B2 | 2/2004 | Sauer et al. | |
| 6,695,786 B2 * | 2/2004 | Wang et al. | 600/461 |
| 6,702,749 B2 * | 3/2004 | Paladini et al. | 600/464 |
| 6,733,458 B1 * | 5/2004 | Steins et al. | 600/461 |
| 6,743,177 B2 | 6/2004 | Ito | |
| 6,755,789 B2 | 6/2004 | Stringer et al. | |
| 6,764,449 B2 * | 7/2004 | Lee et al. | 600/461 |
| 6,951,542 B2 * | 10/2005 | Greppi et al. | 600/443 |
| 7,087,024 B1 | 8/2006 | Pruter | |
| 2002/0156376 A1 | 10/2002 | Wang et al. | |
| 2004/0133111 A1 | 7/2004 | Szczech et al. | |
| 2005/0131291 A1 * | 6/2005 | Floyd et al. | 600/424 |
| 2007/0078334 A1 | 4/2007 | Scully et al. | 600/424 |

FOREIGN PATENT DOCUMENTS

| JP | 2002-102221 A2 | 4/2002 |
|---|---|---|
| WO | 96/32066 A1 | 10/1996 |
| WO | 00/40155 A1 | 7/2000 |

OTHER PUBLICATIONS

Blaivas, Michael, MD, RDMS et al. "*Short-axis versus Long-axis Approaches for Teaching Ultrasound-guided Vascular Access on a New Inanimate Model.*" Acad Emerg Med. vol. 10, No. 12. pp. 1307-1311. Dec. 2003.

Marhofer, P. et al. "*Ultrasound guidance in regional anaesthesia.*" British Journal of Anaesthesia. vol. 94 (1). pp. 7-17. Jul. 26, 2004.

Sites, Brian D. et al. "*The Learning Curve Associated With a Simulated Ultrasound-Guided Interventional Task by Inexperienced Residents.*" Regional Anesthesia and Pain Medicine. vol. 29, No. 6. pp. 544-548. Nov.-Dec. 2004.

Dabu, Anna, BScH et al. *A Practical Guide to Ultrasound Imaging for Peripheral Nerve Blocks*. Copyright 2004 by Vincent WS CHan, MD, FRCPC. pp. 1-83.

"Ultrasound Designed for Vascular Access", iLook 25, Sonosite publication, 2004.

"Sonosite accessories", Produced by Komotion, internet printouts.

European Patent Office, Supplementary Search Report for EP Application No. 06802289.6, dated Oct. 8, 2010.

European Patent Office, European Search Report, Amended Abstract and Search Opinion for European Patent Application No. 11150958.4, dated Jun. 28, 2011.

Japanese Patent Office, Japanese Office Action for Japanese Patent Application No. P2008-529122, dated Sep. 6, 2011.

European Patent Office, European Official Communication for European Patent Application No. 06 802 289.6 dated Sep. 18, 2012.

\* cited by examiner

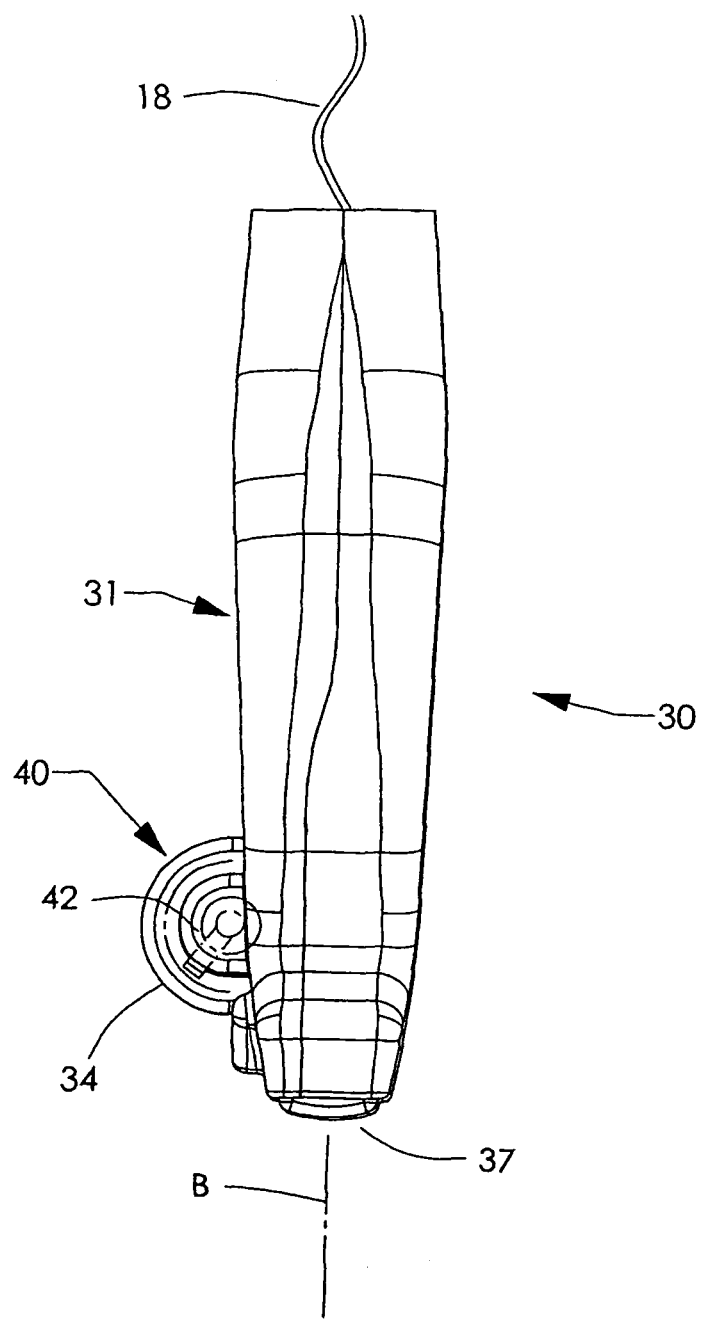

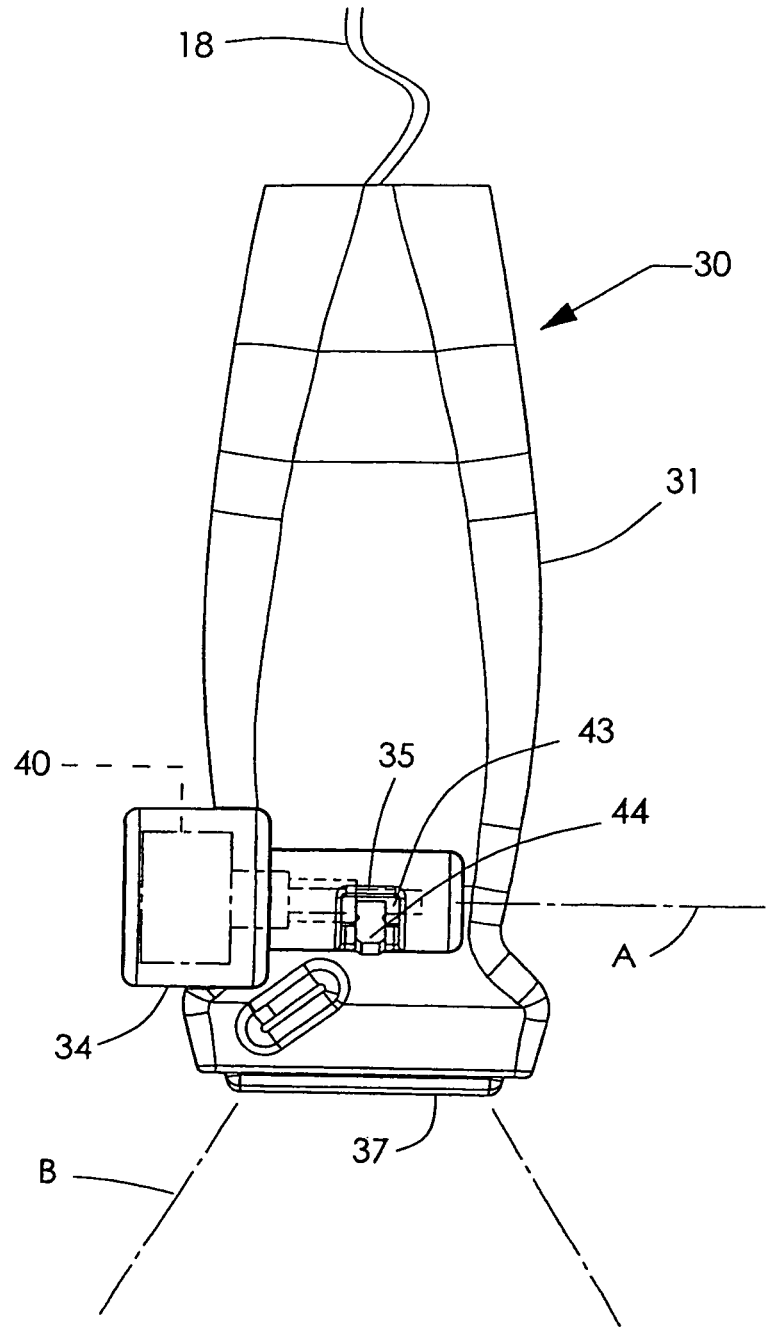

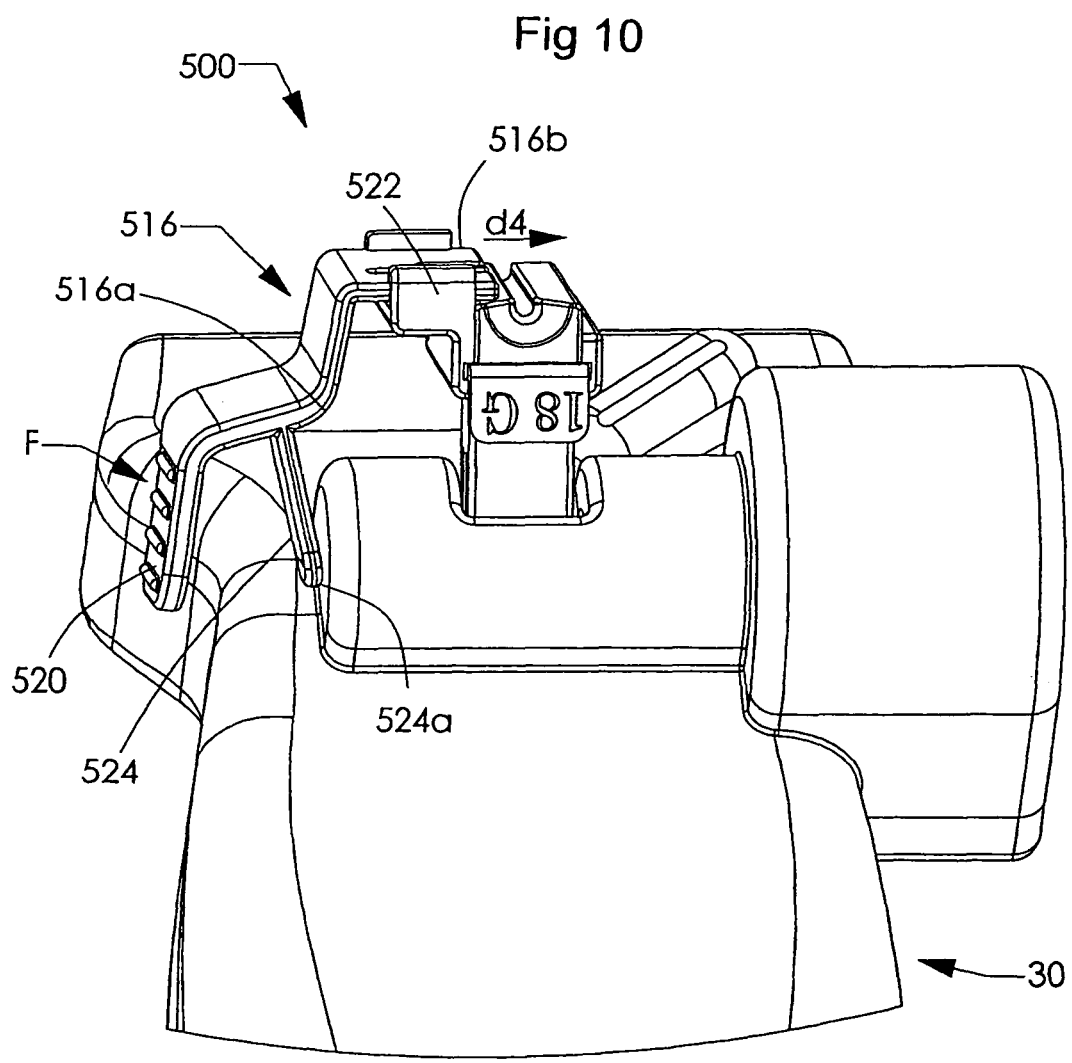

ULTRASOUND GUIDANCE SYSTEM

FIELD OF INVENTION

The present invention relates generally to ultrasound systems and, more particularly, to ultrasound guidance systems. This application claims priority under 35 U.S.C. §119(e) to U.S. Provisional Application No. 60/714,192 filed Sep. 2, 2005 and U.S. Provisional Application No. 60/808,552 filed May 26, 2006.

BACKGROUND OF INVENTION

As an inexpensive and noninvasive technique, ultrasound is useful as a medical imaging modality able to provide real time feedback in a two-dimensional fashion at a patient's bedside. Ultrasound facilitates dozens of procedures performed in hospitals and clinics every day, with these procedures ranging from breast biopsies to central line catheter insertion to amniocentesis.

In a typical ultrasound guided procedure, a doctor will place a small, handheld probe known as a transducer on a patient's skin. The transducer converts electrical energy to acoustic energy. Acoustical energy is transmitted from the transducer and into the patient's body in the form of sound waves. The transmitted sound waves are either reflected back towards the transducer or absorbed by the medium, depending on the acoustical impedance. For example, a bone or fat, having relatively high acoustical impedance, reflects the sound waves with little or no attenuation of the sound wave, while a vein or artery, having a relatively low impedance, will absorb acoustical energy. The reflected sound waves are converted into electrical signals which are used to form a real time two-dimensional image of a portion of the patient's body.

This image may be used to assist a health professional with locating a region of the patient's body for purposes of locating the point where an invasive medical device, e.g., a needle, is inserted. After locating the correct insertion point, the health professional may then begin the medical procedure, such as insertion of a catheter, administration of a local anesthetic, or removal of tissue as in a biopsy.

It is sometimes difficult to accurately track the path and position of the medical device after it has entered the patient's body on the monitor. The medical device, e.g., a needle, is not typically visualized by the ultrasound image, which is essentially a two-dimensional image. Unless the needle is positioned exactly in-plane with the image, the needle is not visible or only partially visible, which means that the needle location or, more importantly the location of the needle tip, is not known exactly. As such, a health professional will often make numerous attempts to insert the device before he or she can see the target tissue mass or blood vessel buckle under the force of the needle pressing against it. And in the case where the target is, for example, a nerve, the health professional often times can only estimate the location of the needle end if it is not visible on the ultrasound image. Such an error-prone, user-dependent procedure is painful for the patient, time consuming for the health professional, and incurs possible additional liability for the hospital with each use. Procedures for using an ultrasound imaging device for peripheral nerve blocks are described in Anna Dabu BScH, and Vincent W S Chan, MD, FRCPC *A Practical Guide to Ultrasound Imaging For Peripheral Nerve Blocks* (copyright 2004 by Vincent W S Chan, MD, FRCPC), the contents of which are incorporated herein by reference in its entirety.

There are multi-planar ultrasound imaging devices capable of producing a three-dimensional image of the body, which may be capable of more accurately locating the position of an invasive medical device, but these types of devices are typically expensive to operate, and require a relatively high degree of skill and training to operate. It would be desirable if a low-cost device, capable of being used effectively by a health professional with moderate or little training in ultrasound imaging techniques, were available which could accurately locate the position of the medical device beneath the skin. This would eliminate much of the "guesswork" that is involved in locating a medical device at the point of interest.

Existing ultrasound devices can be characterized by the approach of the needle-guided insertion with respect to the plane of the ultrasound beam. In the "transverse" type, the medical device, e.g., needle, is orientated out of plane and is sometimes disfavored because visualization of the needle is not reliable as it passes through the patient's body. The "longitudinal" type has the added advantage of seeing the entire length of the needle because it is inserted in plane with the ultrasound beam; however, it can be difficult to keep the needle in the plane of the transducer image due to operator skill and inherent needle-bending when passing through tissue.

While the longitudinal type device is preferred because there is greater chance of tracking the needle, it is also more difficult to position the needle at the target when the needle is planar with the image. A transverse needle pathway, on the other hand, is more intuitive, is shown to be easier for novice ultrasound users, and is the preferred approach for various procedures according to experts. The following three studies have been conducted which compare the performance of longitudinal verses transverse type of ultrasound guidance devices, all of which are incorporated herein by reference: P. Marhofer, M. Greher and S. Kapral, *Ultrasound guidance in regional anesthesia*, British Journal of Anasthesia 94 (1): 7-17 (2005); M. Blaivas, L. Brannam, and E. Fernandez, Short-axis verses *Long-axis Approaches for Teaching Ultrasound-guided Vascular Access on a New Inanimate Model*, ACAD Emerg Med, Vol. 10, No. 12 (December 2003); and B. D. Sites, J. D. Gallagher, J. Cravero, J. Lundberg, and G. Blike *The Learning Curve Associated With a Simulated Ultrasound-Guided Interventional Task by Inexperienced Anesthesia Residents*, Regional Anesthesia and Pain Medicine, Vol. 29, No. 6 (November-December 2004), pp. 544-548.

One known ultrasound device for assisting a health professional with needle placement in a body is the Ilook™ personal imaging tool, sold by SonoSite, Inc., which includes a series of removable needle guides. The device is used to place a needle at a target location beneath the skinline by real-time visual identification of the target via an ultrasonic image. A bracket, located on the front of the transducer, is used to mount a needle guide. The needle guide is orientated such that a needle received therein will extend approximately perpendicular to the sonic scanning plane. Thus, the SonoSite, Inc. device is a transverse-type device. When it is time to perform the procedure, the device is wrapped in a sterile sleeve (an acoustic coupling gel is put into the sleeve and the sleeve is placed over the transducer) and the sleeve is sealed using a rubber band. The sleeve covers the transducer and bracket. The procedure for use includes inserting the acoustic coupling gel into the sleeve, covering the device with the sleeve, ensuring there are no cuts or tears in the sleeve, then securing the sleeve with a rubber band. After this sterilization of the transducer, a sterile needle guide is snap-fit on the bracket. There is more than one-type of needle guide to choose from. The choice depends upon the distance between the skinline and the top of the vessel. Three choices are available for this particular device: a 1 cm, 2 cm and 3 cm needle guide that reflect an approximate depth of the target vessel beneath the skinline. These different lengths correspond respectively to increasing angular inclinations of the needle relative to the skinline.

The needle guide has a door that can be locked in a closed position by a slidable switch, thereby retaining the needle shaft between the door and a semi-circular recessed area. The needle is placed in this recessed area and the door is closed to hold the needle therein. The transducer with needle is then placed on the skinline and the top of the vessel is located via the sonic image. The needle is then inserted into the body.

After the needle has reached the target, the transducer needs to be removed from the needle, which requires unlatching the door of the needle guide. This procedure can cause complications as it is often necessary to maintain precise positioning of the needle within the body. When the door is being unlatched, there can be unacceptable motion of the transducer (and therefore of the needle) as a result of overcoming mechanical resistance in the latch.

Another known ultrasound imaging device is the Site-Rite® Ultrasound System by Bard Access Systems. This device also provides a needle guide to hold the needle at a fixed angle with a transverse approach and is operated in a similar manner as the SonoSite, Inc. device described above. A health professional first places the transducer such that a target of interest (e.g. a vessel's lumen) is visible on the screen. The location of the target is then estimated and a needle guide is selected such that the needle will pass closest to the target's location. Because the entire probe is enclosed in a sterile sleeve, the needle guide is typically disposable and kept sterile until use. When needed, the needle guide is clamped to the probe through the sterile sleeve. Each needle guide is set to a static angle which is not adjustable. If the insertion angle needs to be corrected, the needle guide must be removed and substituted with a different needle guide. Additionally, after inserting the needle into the target, the probe must be rocked to pry the needle from the needle guide, potentially disrupting the needle-target interaction. This is because the needle guide is a one piece needle guide with lips that are flexed to release the probe from the needle.

U.S. Pat. No. 6,695,786 discloses a longitudinal-type ultrasound device for biopsy procedures. The device has a biopsy needle guide coupled to an ultrasound probe. The needle guide has a needle holder connected to the probe by a link assembly that allows a user to rotate the biopsy needle, but without allowing the user to twist or bend the needle outside the imaged plane. Other examples of longitudinal-type devices are described in U.S. Pat. No. 4,058,114 and U.S. Pat. No. 4,346,717.

Known ultrasound monitors are typically fixed to a stand. In these systems, a health professional often must turn his or her head to focus on the screen. Also, these devices have cords connecting the ultrasound probe to the monitor which are typically much longer than needed for most procedures because it must be sufficiently lengthy for extreme cases. As a result, the cord can often obstruct the probe's user. Additionally, the probe cannot be maintained in a sterile condition when it is placed on a holder provided with the system.

There is a need for a user-friendly ultrasound system that requires only a relatively low-degree of training and/or skill in ultrasound imaging techniques. It would also be desirable to have a device that reduces the error rate and/or discomfort to the patient when locating targets during invasive procedures, and that offers health professionals the ability to direct needles to a target of any depth when the needle is controlled in a plane perpendicular to the scanning plane. It would also be desirable to have a device that is capable of being used in any invasive procedure without additional health costs charged by a health provider; a device that can be pre-aimed at a target and before insertion into a living body; a device that provides easy visibility of the ultrasound image and medical device in real time; and a device that is adapted for releasably fastening an invasive medical device to a probe or imaging device so as to reduce incidences of displacement of the medical device within the patient's body when the medical device is separated from the probe or medical device.

SUMMARY

The present invention is directed to an ultrasound needle guidance system that facilitates placement of an ultrasound monitor over a patient and ensures accurate and simple needle placement in a target of interest within a patient's body. According to an embodiment of the invention, a hand-held ultrasonic probe includes a needle guidance position that holds a needle. The needle is orientated transverse to the scanning plane of the transducer. The needle can be rotated through a continuous range of angles and these angular changes can be tracked and displayed as a cross-hair (or other type of visual indicia) on a nearby monitor screen with the ultrasonic image. In this way, a health professional can accurately track and locate a needle to ensure precise placement at a target within a patient's body.

In another embodiment, an ultrasonic probe includes a hand-held body, a transducer contained within the body and adapted for generating ultrasonic images of a scanning plane, and a needle guide coupled to the body and rotatable about an axis that is in a plane parallel to the scanning plane. The probe may include a position detector for detecting the rotation of the needle.

In another embodiment, an ultrasonic probe includes a hand-held body, a transducer contained within the body and adapted for generating ultrasonic images of a scanning plane, a shaft mounted within the body and configured to rotate through an angle that is in a plane transverse to the scanning plane, a position detector coupled to the shaft, and an arm configured to receive a needle holder, connected to the shaft and extending out of the body. The body may be a sterile shell of a body that holds the transducer. The arm may be restricted to rotate within a transverse plane.

In another embodiment, an apparatus for tracking the position of a needle relative to an ultrasonic image includes a hand-held ultrasonic probe having a scanning plane, a needle guidance portion including a needle holder coupled to the probe for rotation about an axis that is in a plane parallel to the scanning plane, the needle holder defining a needle path originating at the needle holder and extending through the scanning plane, and needle path data generated by the needle guidance portion, wherein the needle path data locates the intersection of the needle path and the scanning plane.

In another embodiment, a method for positioning a needle for treatment of a target body within a patient using a hand-held ultrasonic probe having a scanning plane is provided. This method includes the steps of mounting a needle on the probe, the needle having an angular position relative to the scanning plane, placing the hand-held probe on the patient, displaying a two-dimensional image of the scanning plane including the target body, the image including a visual indicia of the needle position relative to the target body, rotating the needle about an axis that is in a plane parallel to the scanning plane while monitoring the corresponding movement of the visual indicia, and when the needle is aligned with the target body, placing the needle at the target body. According to this method, the needle may be placed at the target by rotating the needle while tracking the movement of a visual indicia of the needle's pathway on a display screen. Once the visual indicia aligns with the target, the needle is positioned appropriately for placement at the target.

In another embodiment, a method of tracking the position of a needle relative to a target body includes the steps of providing a hand-held ultrasonic probe having a scanning plane, mounting a needle on the probe, the needle defining a needle path extending from the needle to the scanning plane, rotating the needle guide in a plane transverse to the scanning plane, and generating data locating the intersection of the needle path and the scanning plane in response to rotation of the needle guide. This method may include the step of computing for a continuum of angles through which the needle rotates the intersection of the needle path and the scanning plane.

In another embodiment, a system for locating a needle insertion point includes a display, a hand-held ultrasonic probe defining a scanning plane, an ultrasonic image of the scanning plane, generated by the probe and displayed on the display, a needle guide coupled to the probe for rotational motion relative to the probe and about an axis that is in a plane parallel to the scanning plane, a position detector coupled to the needle guide, position data generated from the position detector; and a visual indication of the needle position generated from the position data and displayed with the ultrasonic image on the display device.

In a preferred embodiment, the ultrasound system comprises a height adjustable stand, an adjustable and moveable ultrasound monitor, a retractable cord, and a system of hooks allowing probe sterility while mounted on the ultrasound machine. Connected to the ultrasound monitor is an ultrasound probe.

Preferably a removable sterile clip is used to mount the needle to the probe. In this aspect of the invention, the clip is configured to minimize mechanical noise associated with removal of the probe from the needle. As such, it is preferred to use a clip that does not rely on a mechanical engagement to retain the needle in the needle clip.

In another embodiment of the invention, an ultrasonic probe includes a needle clip that has a cradle for a needle and an arm having a first end coupled to the cradle and a second end forming a cover. In this embodiment, the cover is manually movable between a first position opening the cradle and a second position closing the cradle. Also, the cover is detached from the cradle in the second position and when the cover is in the second position, the cover and cradle together form a passageway for a needle shaft disposable between the cover and cradle such that the passageway allows movement of the needle in a first direction and substantially prohibits movement of the needle in a second direction that is perpendicular to the first direction.

In another embodiment of the invention, a method of releasably fastening a needle to an ultrasonic probe includes the steps of providing a needle clip on the probe, the needle clip including a displaceable arm and a cradle adapted to receive a needle shaft, placing the needle shaft within the cradle, applying pressure to the arm such that the arm moves from a first position distal of the cradle to a second position proximal to and mechanically decoupled from the cradle, whereupon the needle is held between the cradle and arm, and relieving the pressure on the arm, whereupon the arm moves from the second position to the first position. Alternatively, finger pressure may move the arm away from the cradle so that when the finger pressure is relieved, the needle is retained within the cradle.

Preferably, the ultrasound probe is encompassed by a thin plastic sterile shell that allows access to a connector for mounting the needle clip.

In still another embodiment, an apparatus for tracking the position of a needle relative to an ultrasonic image includes a hand-held ultrasonic probe having a scanning plane, a needle guidance portion including a needle holder coupled to the probe for rotation about an axis that is in a plane that is non-parallel with the scanning plane and perpendicular to a body surface to be penetrated by a needle received in the needle holder. For example, the axis may lie in a plane that makes at least a 10, 15, 30, 45, 60, 75, between 45 and 90 degree, or up to 90 degree angle with the scanning plane.

In another embodiment of the invention, a sterile shell for an ultrasonic probe includes a first shell portion, a second shell portion, a third shell portion defining a chamber for receiving an end of the ultrasonic probe. Living hinges may be used to rotatably connect the first, second and third shell portions together. Additionally, an acoustic coupling gel may be contained within the chamber and sealed until use by a removable lidstock, e.g., a plastic wrapper or foil.

In another embodiment of the invention, a method of sterilizing an ultrasonic probe includes the steps of providing a sterile shell, including a first, second and third shell portion connected to each other by living hinges, the third shell portion defining a chamber containing a gel, removing a cover from the third shell portion, placing a waveguide of the probe inside the third shell portion, and placing the second and first shell portions over the probe, thereby enclosing the probe within the shell.

Among the various advantages apparent from the description, there is provided a particularly useful apparatus and method for administering a nerve block or performing an acute angle catheter entry procedure.

These and other aspects of the present invention will become apparent to those skilled in the art after a reading of the following description of the preferred embodiment when considered with the drawings.

BRIEF DESCRIPTION OF THE DRAWINGS

FIG. 4 is a side view of the ultrasound probe and sterile shell of FIG. 1A.

FIG. 5 is a front view of the ultrasound probe and sterile shell of FIG. 1A.

FIG. 10 is a perspective view of a third embodiment of a needle clip attached to the probe of FIG. 5 according to an embodiment of the present invention.

DETAILED DESCRIPTION OF THE PREFERRED EMBODIMENTS

Figure 1A:
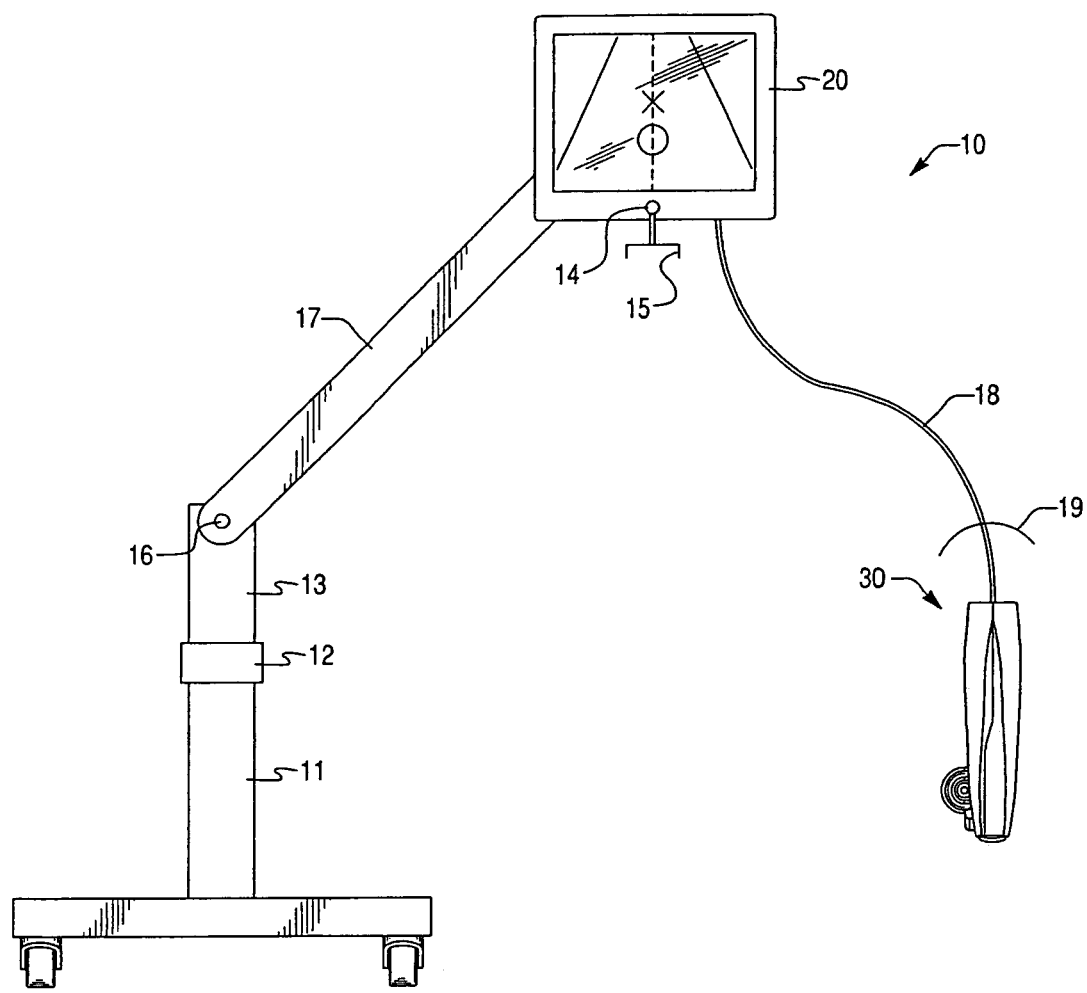
FIG. 1A is a front view of a ultrasound guidance system according to an embodiment of the present invention.

Referring now to the drawings in general, the illustrations are for the purpose of describing preferred embodiments of the invention and are not intended to limit the invention thereto. FIG. 1A shows a preferred cart-based compact ultrasound needle guidance system 10. Among the features of system 10 is a monitor 20 (preferably an LCD monitor) that can be easily positioned for optimal viewing during an ultrasound imaging process, and an ultrasonic probe 30 that sends ultrasonic image data to monitor 20 via a cord 18. Probe 30 is preferably encased in a sterile shell 31 that completely encloses probe 30. Probe 30 includes a needle guidance device, rotatably mounted to probe 30, which enables a health professional to make angular adjustments to a needle mounted to probe 30 during a procedure. Angular adjustments to the needle are displayed on monitor 20 in real time with the ultrasonic image so that the needle position can be tracked and aligned precisely with the target located within the patient.

System 10 is lightweight, so that it may be moved about without great difficulty. A stand 11 supports system 10, which may include wheels to move it about the floor. Stand 11 is connected to a height adjustable pole 13 which is connected at its upper end to a rotatable arm 17. A tightening collar 12 fixes pole 13 at a desired height and a lockable pivot 16 fixes arm 17 at a desired angle relative to pole 13. Thus, in preparing system 10 for an ultrasound procedure, monitor 20 is movable such that it can be positioned directly in front of the user and over the patient. This is accomplished by adjusting the height adjustable pole 13 and pivoting the rotatable arm 17 about the lockable pivot. Once the desired height is reached, height adjustable pole 13 and arm 17 are locked into position by tightening collar 12 and pivot lock 16, respectively. The mobility and lightweight properties of system 10 lend itself to easy height and angular adjustments by a single health professional.

System 10 is designed to avoid occurrences of "drift" during an invasive medical procedure using an ultrasound imaging device. When a health professional must switch his or her attention from the patient's body to the monitor (so as to track the progress of the needle), the ultrasound device can become misaligned. System 10 avoids occurrences of drift by allowing selective placement of the monitor in a position so that the health professional may maintain his or her immediate attention on the patient and the position/orientation of the ultrasonic probe 30 while viewing an ultrasound image on monitor 20. Thus, system 10 may be operated so that the probe and patient are within the same field of view as the ultrasound image. This can reduce error rates, improve the accuracy of the scan and or insertion of a needle and thus reduce the discomfort to the patient and time taken for an invasive medical procedure.

When arm 17 is moved and locked in place, monitor 20 may require further adjustment so that the image appears in the correct orientation relative to probe 30. This can be accomplished in one of two ways. The ultrasound image may be oriented electronically by rotating the image on the screen, or monitor 20 may be repositioned by providing a pivotal mount for monitor 20 on arm 17 so that monitor 20 may be tilted relative to arm 17. Either or both of the above approaches may be followed in order to facilitate adjustability of the image so that a health professional may obtain an optimal viewing orientation of the ultrasound image.

Figure 1B:
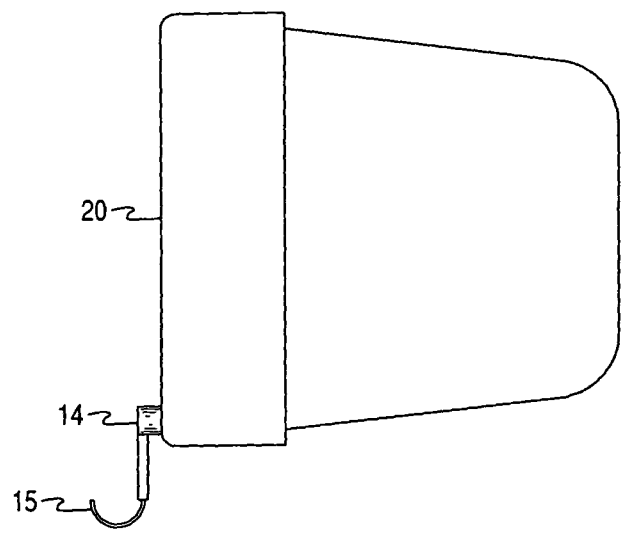
FIG. 1B is a side view of a monitor of the system of FIG. 1A.

Cord 18 is retractable within monitor 20 using a spring-and-ratchet or similar mechanism. This allows cord 18 to be pulled in and out of monitor 20 to a desired length. Alternatively, a wireless communication link may be substituted for cord 18. In this embodiment, probe 30 may further include a portable and replenishable power source such as a rechargeable battery. Referring to FIG. 1B, a latch or hook 15 is mounted to monitor 20 and pivotal about a rotatable mount 14. Probe 30 may be stored and maintained in a sterile condition on hook 15 when not in use. A ring or other suitable latching structure may be provided on cord 18 near probe 30 for latching to hook 15. If a wireless probe is used, then a suitable latching device may be provided at the upper end of probe 30. Hook 15, being mounted to a free pivot 15 that is rotatable within the plane of the monitor screen, allows a latched probe 30 to hang in a vertical position from monitor 20 regardless of monitor 20 orientation. With this arrangement, system 10 provides a convenient location for storing probe 30 when it is not needed, minimizes movement and operator error during a procedure, and yet still maintains probe sterility.

FIGS. 4 and 5 illustrate side and front views, respectively, of probe 30. Probe 30 includes an ultrasound transducer, which generates the image data transmitted to monitor 20. This image data is used to generate real time images of the patient's body below the skinline. As shown, probe 30 is preferably encased within a sterile shell 31 when performing a procedure. This ensures sterility during a procedure. A sterile sleeve may also be used. In an alternative embodiment, a sterile sleeve may be secured at an upper end of probe 30 and extend upwardly to enclose cord 18. This sleeve may be included with shell 31 or attached separately. As described in greater detail, below, the transducer is conveniently encased within sterile shell 31 by enclosing the transducer between front and rear shell parts, and a front part which encloses the forward end, i.e., the area designated by 37 in FIG. 5.

Probe 30 may be equipped with any suitably chosen, commercially available transducer. For example, probe 30 may be configured as a linear or curved array type and may be adapted for scanning within high frequency bandwidths (e.g., 10-15 MHz) for viewing near the skin surface or low frequency bandwidths (e.g., below 5-7 MHz) for viewing well below the skin surface. Ultrasonic image data can be generated and processed for display on monitor 20 using any suitably chosen ultrasound system.

Acoustic signals are transmitted/received through a lower surface 37 of the transducer such that a scanning plane B covers an area below probe 30 as illustrated in FIGS. 4 and 5. At a lower end of probe 30 there is a needle guidance portion 40. Needle guidance portion 40 is used to mount a needle to probe 30 and permits a health professional to make continuous angular adjustments to the needle relative to scanning plane B during an ultrasound procedure. Thus, system 10 does not require a health professional to pre-select an angular orientation of the needle. Rather, a precise angular orientation can be determined while an image is generated of the area beneath the skin.

Figure 5A:
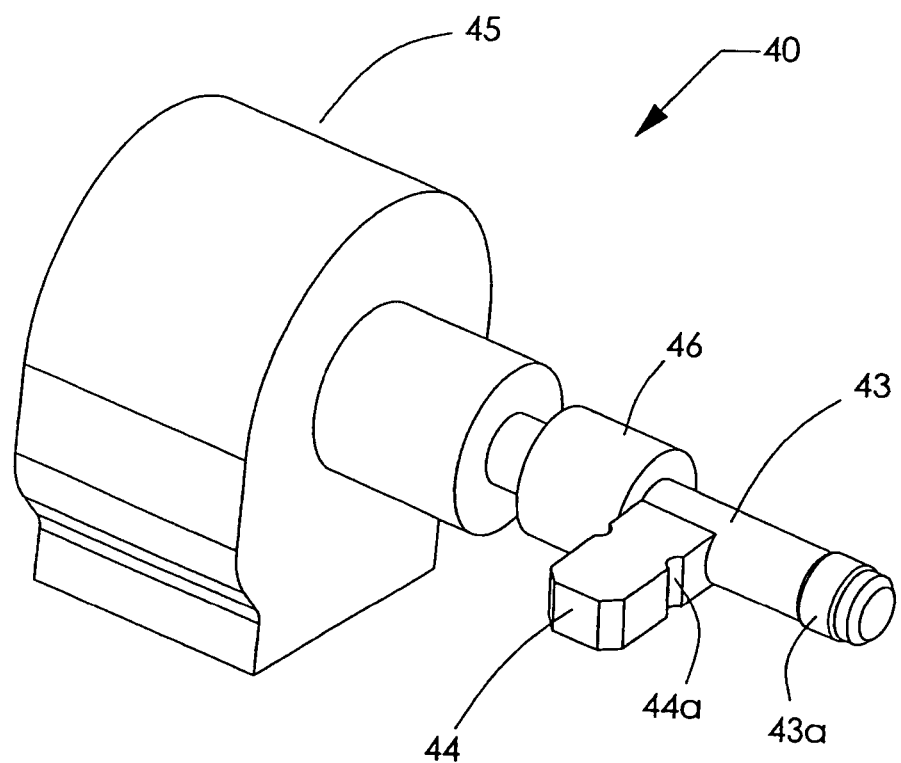
FIG. 5A is a perspective view of a portion of a needle guidance portion of the system of FIG. 1A.

As seen in FIG. 5A, needle guidance portion 40 includes a rotatable shaft 43 and a clip connector 44 extending perpendicularly from shaft 43. Clip connector 44 extends through an opening 35 formed on shell 31 so that it may releasably receive a needle clip, e.g., needle clip 200 shown in FIG. 8C. The needle is then mounted to needle clip 200. When mounted to needle guidance portion 40, the needle may be rotated through a continuum of angular positions relative to scanning plane B. In particular, needle guidance portion 40 is arranged so that angular positions of the needle are measured about an axis that lies in a plane parallel to scanning plane B. Hence, probe 30 is configured for selectively positioning a needle in a plane transverse to scanning plane B.

Figure 8A:
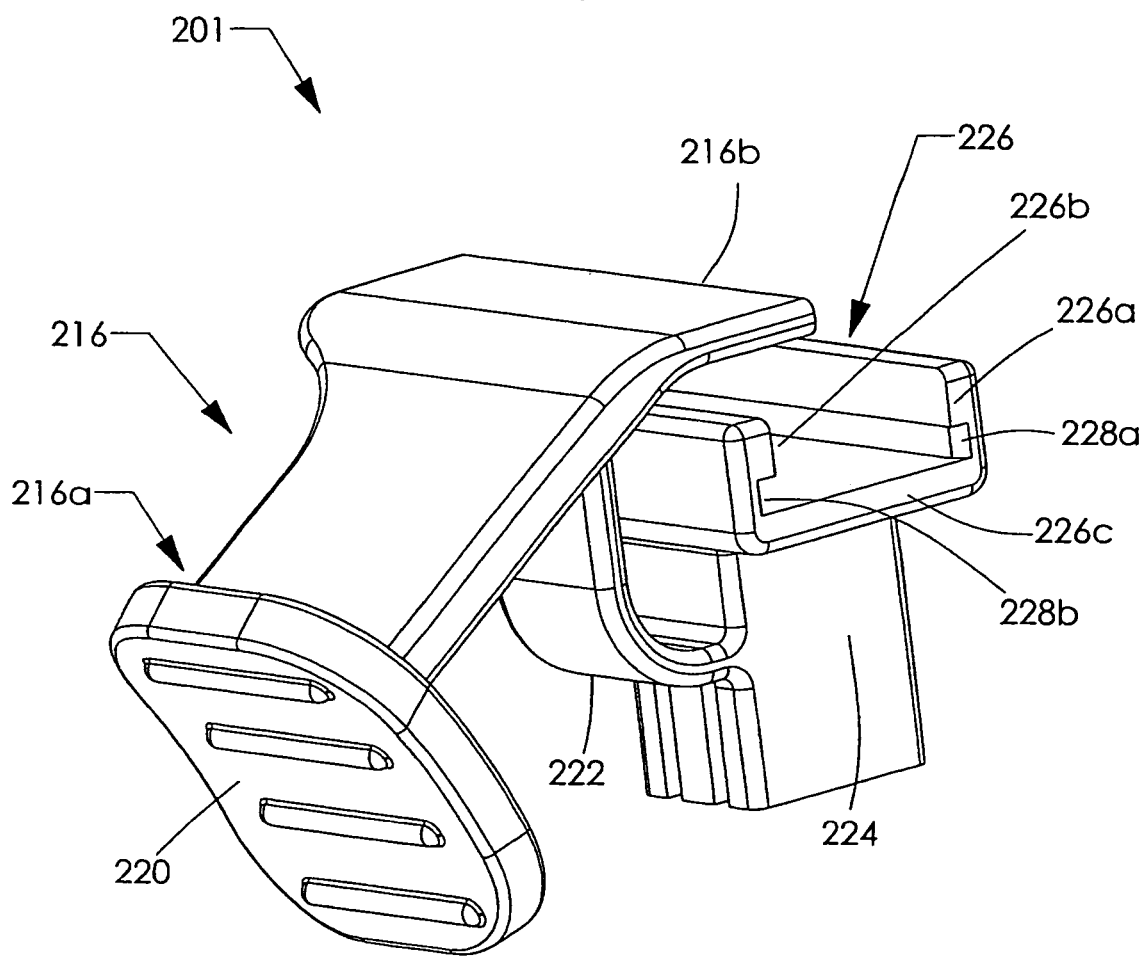
FIGS. 8A and 8B are first and second perspective views of first and second parts of a first embodiment of a needle clip according to the present invention.
Figure 8B:
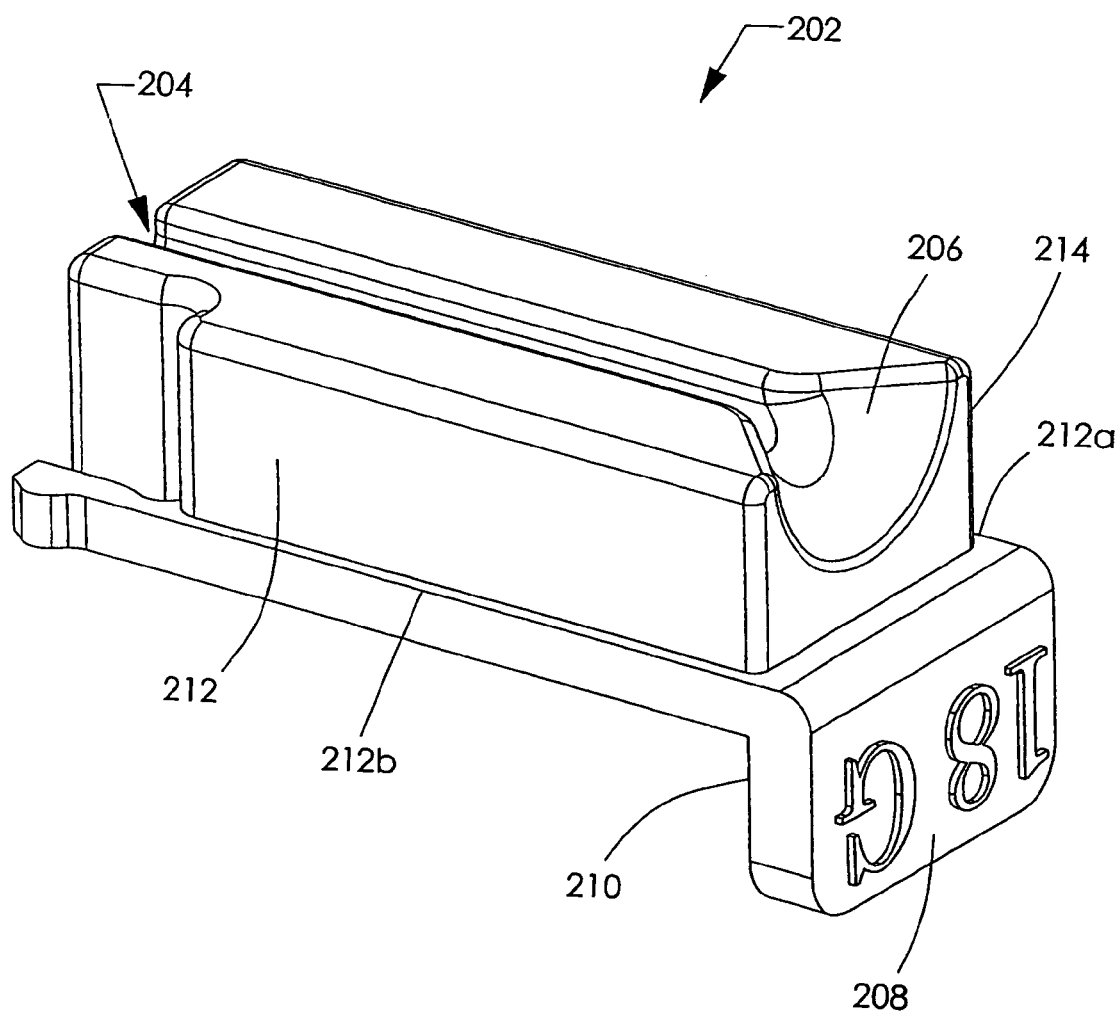
Figure 8C:
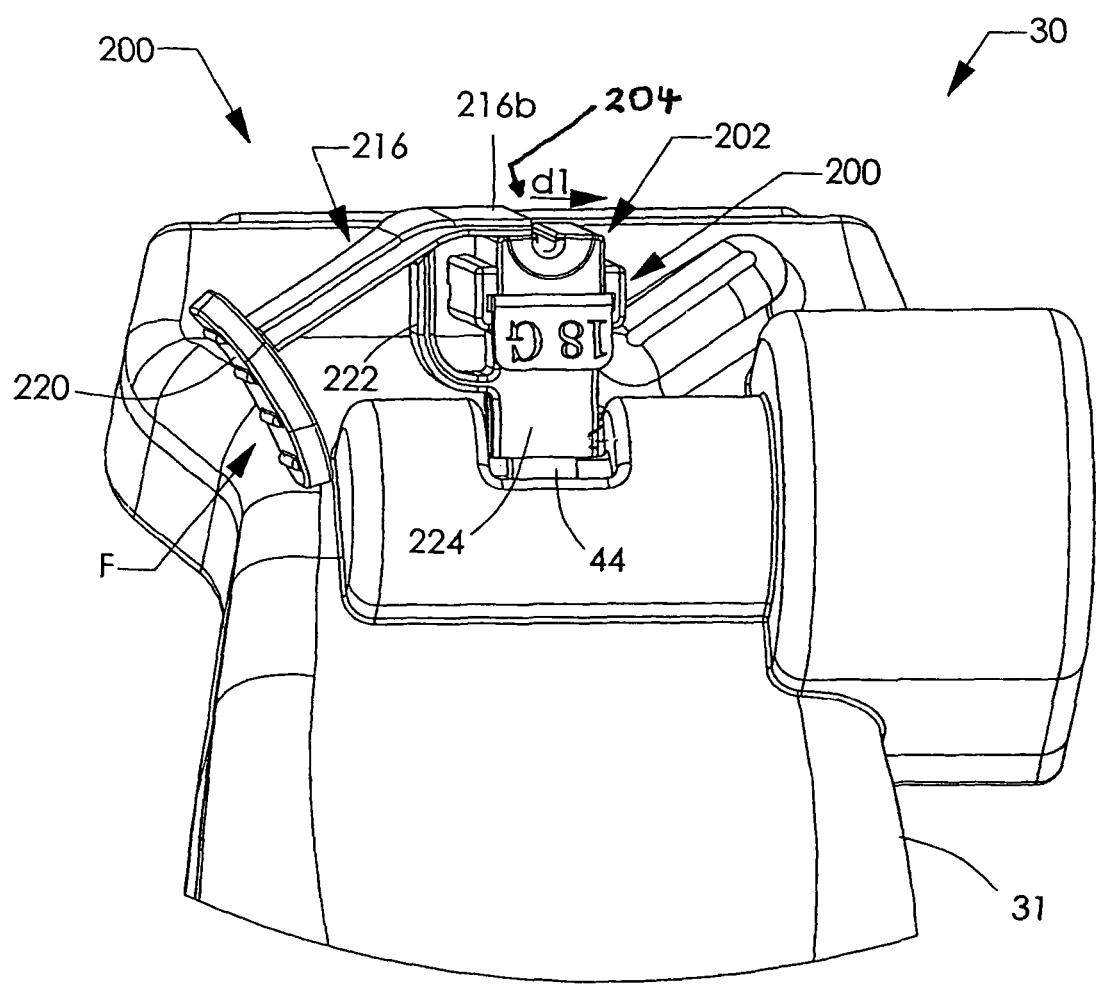
FIG. 8C is a perspective view of the needle clip of FIGS. 8A and 8B attached to the probe of FIG. 5.

With reference to FIGS. 5, 5A and 8C, shaft 43 includes a bearing 43a that is received within a housing 34 of shell 31. This housing 34 permits rotational motion of shaft 43 and hence clip connector 44 about an axis A (FIGS. 5 and 5A), which lies in a plane parallel to scanning plane B. An opening 35 is formed on housing 34 so that clip connector 44 may extend out from shell 31 and rotate through a predetermined range of angles. In another embodiment, clip connector 44 may be disposed so that it is inset from, or flush with opening 35 of shell 31. This embodiment may be preferred since clip connector 44 is fixed to probe 30 and hence not sterile. By having clip connector 44 recessed within opening 35, potential contamination of shell 31 may be avoided.

A needle clip 200 is attached to clip connector 44 by placing clip connector 44 within a hollow post 224 formed on needle clip 200 and engaging a snap-fit provided by depressions 44a formed on clip connector 44 and mating ledges formed on inner surfaces of post 224. Other means may be used for disengagably mounting clip 200 to clip connector 44. Needle clip 200 may also include a skirt formed near a lower end of post 224. The skirt is intended to cover opening 35 when needle clip 200 is mounted to clip connector 44, without obstructing rotation of needle clip 200 about probe 30, so as to further reduce the chance of contamination during a procedure. A shaft of the needle is received in a cradle portion 204 of needle clip 200 and releasably held therein by a fastening arm 216 during the procedure. The snap-fit engagement between post 224 and clip connector 44 is preferably easily releasable so as to enable a health professional to remove needle clip 200 from clip connector 44 after a procedure is completed. It is preferred that needle clip 200 is a disposable needle clip and thus replaceable after every procedure to maintain sterility. Needle clip 200 is placed on clip connector 44 after the transducer of probe 30 has been wrapped in a sterile sleeve or encased within a first embodiment of a sterile shell 31 as shown in FIG. 5.

In the preferred embodiments, needle guidance portion 40 includes a needle tracking device that tracks the angular position of the needle as it rotates about axis A. For example, in the embodiment illustrated in FIG. 5A, a potentiometer 45 is rotatably coupled to shaft 43 and used to determine angular displacements (or velocities) of a needle as it rotates about axis A. Shaft 43 is coupled to potentiometer 45 by, e.g., engaging a threaded end 46 of shaft 43 with a rotor portion of potentiometer 45. It will be appreciated that any suitably chosen, commercially available tracking device may be used in place of potentiometer 45. For example, shaft 43 may be coupled to a position encoder for detecting angular motion of shaft 43. In another embodiment, needle rotation relative to probe 30 may be accomplished using a living hinge. Potentiometer 45 illustrated in FIG. 5A is part of a potentiometer circuit (not shown) that transmits electronic signals to a processor. These signals are used to produce real-time video images of the needle's angular position relative to scanning plane B. Position data from the potentiometer circuit may be transmitted to monitor 20 separately from signals transmitted by the transducer, or they may be combined into one signal. In one embodiment, angular position data is processed separately from data from the transducer using software associated with monitor 20 or a separate computer connected to monitor 20. This software produces a real-time, continuous image of the needle orientation that is superimposed over the ultrasound image. In other embodiments, transducer and angle measuring data may be processed simultaneously so as to produce a single data stream that is fed to monitor 20. The software used to process needle position information may be incorporated into probe 30 or reside at a separate computer.

Figure 5B:
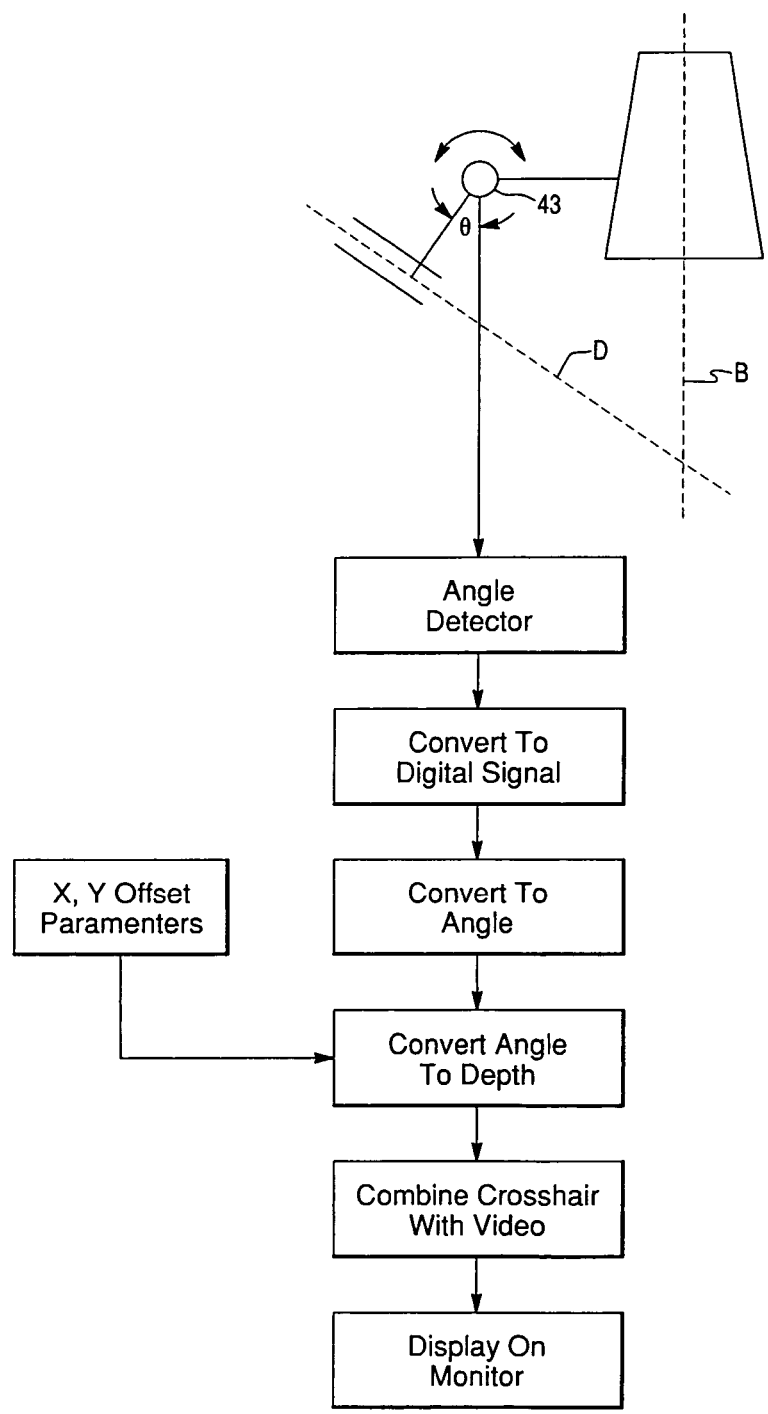
FIG. 5B is a schematic illustration of the processing steps for needle positioning data according to an embodiment of the present invention.

The schematic illustration of FIG. 5B describes one embodiment of the steps that may be used to convert movement of the needle mounted to probe 30 into a video image on monitor 20. As shown, needle rotation through an angle θ is detected by the angle detector, which in this example is a potentiometer. The analog signal produced by potentiometer 45 is converted into a digital signal. A digital position encoder may be used in place of potentiometer 45. The digital signal is then converted into an angle based upon stored potentiometer calibration data. This angle data is then converted into a depth relative to the ultrasonic image using stored X, Y offset parameters. These parameters are obtained from calibration data and reflect the offset position of the needle relative to scanning plane B. The depth position is then combined with the ultrasonic image data and displayed on monitor 20, e.g., the cross-hair 62a illustrated in FIGS. 2 and 3.

Figure 2:
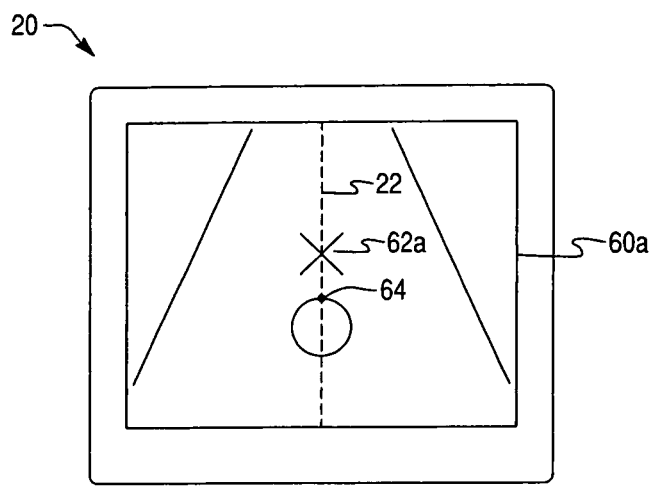
FIG. 2 is a first front view of the monitor of FIG. 1B showing an image generated by an ultrasound device and a cross hair indicating a first angular orientation of a needle mounted to an ultrasound device.
Figure 3:
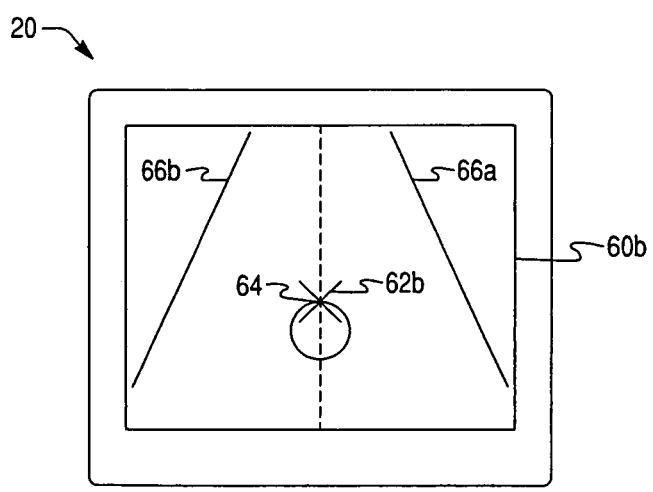
FIG. 3 is a second front view of the monitor of FIG. 1B showing the same image generated by an ultrasound device and a cross hair indicating a second angular orientation of the needle.
Figure 3A:
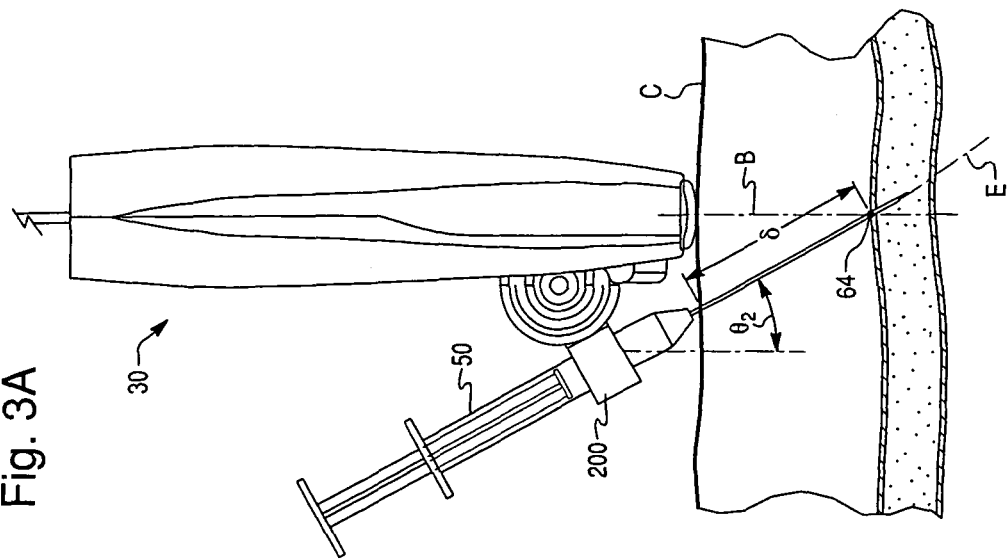
FIG. 3A is a second side view of the ultrasound probe of FIG. 2A and needle mounted thereto corresponding to the monitor image of FIG. 3, with the probe placed on the patient and after the needle has been placed at a target within the patient and the probe is enclosed in a sterile shell.
Figure 2A:
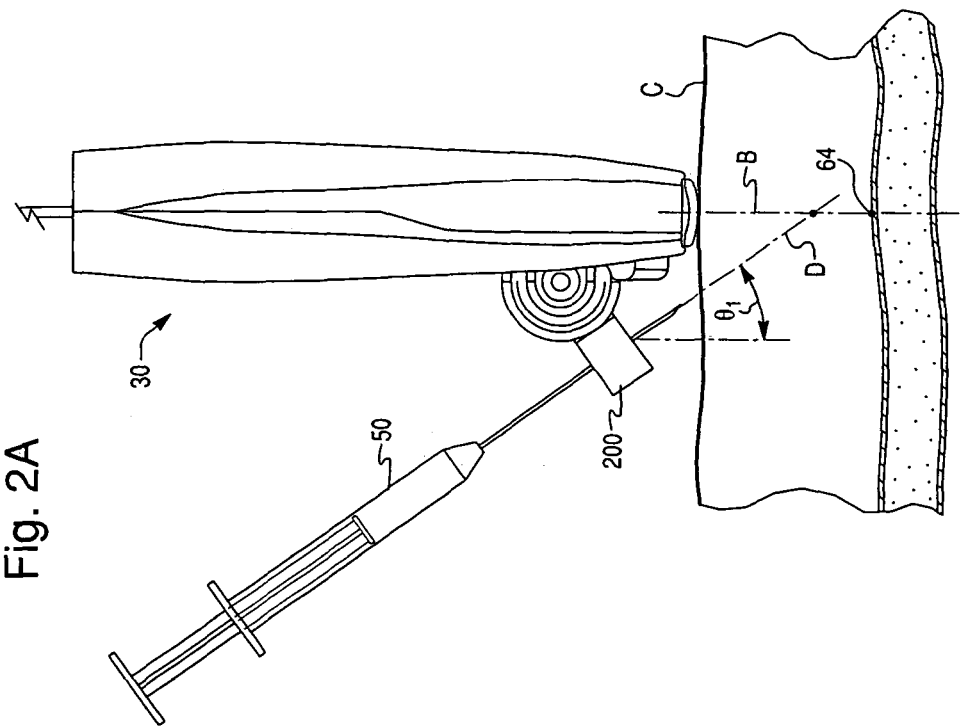
FIG. 2A is a first side view of an ultrasound probe of the system of FIG. 1A and needle mounted thereto corresponding to the monitor image of FIG. 2, with the probe placed on a patient and prior to inserting the needle into the patient and the probe is enclosed in a sterile shell.

Operation of probe 30 in connection with monitor 20 will now be described with reference to FIGS. 2, 2A, 3 and 3A. FIGS. 2A and 3A illustrate side views of probe 30 with needle clip 200 secured to clip connector 44 and a needle 50 received in needle clip 200. Probe 30 is encased in sterile shell 31. A tip of needle 50 is positioned adjacent to, but not penetrating the patient's skinline C in FIG. 2A whereas in FIG. 3A the shaft of needle 50 is inserted into the patient and properly located at target 64. FIG. 2A shows needle 50 orientated at a first angle $\theta_1$ relative to a scanning plane B of the transducer and FIG. 3A shows needle 50 orientated at a second angle $\theta_2$ relative to scanning plane B. Dashed lines D and E represent the pathways for needle 50 when orientated at the respective angles $\theta_1$, $\theta_2$ and distance δ in FIG. 3A is the distance along pathway E from the skinline C that needle 50 must be inserted in order to reach target 64. The term "needle pathway" refers to the path needle 50 will take if inserted into the patient's skin at a given angle relative to the scanning plane B. As can be seen in FIG. 2A, needle pathway D intersects plane B above the intended target 64 when orientated at angle $\theta_1$. If needle 50 is inserted at this angle, needle 50 will miss target 64. However, when needle 50 is orientated at angle $\theta_2$ relative to scanning plane B, needle 50 will follow needle pathway E and intersect scanning plane B at the target 64.

It is desirable to have both the correct needle pathway and insertion depth identified before needle 50 is inserted. This will minimize discomfort to the patient (caused by adjustments to the needle position after the needle has penetrated the skin) and/or simplify the process of positioning a needle at a target, which reduces the skill level and time needed to place a needle at target 64. Moreover, it is important to know the depth of needle insertion as this will increase the chances for effective administration of the needle contents at a target and ensure that the needle tip does not cause undue damage to neighboring tissue.

At present, the health professional often times has to rely solely upon an ultrasound image of the living body, e.g., tissue deformation such as buckling of a blood vessel wall, when deciding whether or not the needle has reached the intended target. In cases where there is no change in the ultrasound image of the living body to indicate a needle location, e.g., when applying a local anesthesia to block a nerve, a health professional must rely on his or her knowledge of the patient's anatomy, which is only an approximation. If a health professional could obtain accurate information of both the needle pathway, target location and the actual insertion depth of the needle, then the needle can be more precisely placed at the target.

System 10 is configured to provide a health professional with a visual indication of the needle pathway needed to intersect plane B at the target 64 and the insertion depth needed to place the tip of the needle at the target 64 (insertion distance δ). FIGS. 2 and 3 show images 60a and 60b, respectively, generated on monitor 20 that correspond respectively to the position of probe 30 and needle 50 illustrated in FIGS. 2A and 3A. Cross hairs 62a and 62b indicate the point of intersection between the respective needle pathways D and E and scanning plane B. A cross section of a blood vessel wall is also shown in FIGS. 2 and 3 with a section of the vessel wall corresponding to target 64. Image 60a indicates that the needle pathway D will intersect plane B above target 64 (cross hair 62a), which means that needle pathway D is too shallow. Image 60b indicates that the needle pathway will intersect plane B at target 64 (cross hair 62b covers target 64), which means that needle pathway E is the correct pathway for needle 50.

The insertion distance δ for needle 50 may be obtained from the insertion angle $\theta_2$ and other known distances which may be stored with the X, Y Position Parameters discussed earlier. For example, the insertion depth may be determined from $\theta_2$, the distance from surface 37 and target 64, the horizontal distance between the needle shaft centerline (at the needle clip) and the scanning plane B and the vertical distance between the needle shaft centerline (at the needle clip) and the bottom surface of probe 30. Once obtained, the needle insertion depth may be matched to distance δ by providing score lines on needle 50 or a stopper member that prevents needle 50 from being inserted beyond the desired depth. For certain procedures, the health professional may not need to know δ in order to ensure accurate placement. For example, if needle 50 is intended for a blood vessel wall, a visually identified buckling of the vessel wall, flow of blood through the needle shaft passage or change in resistance to needle 50 penetration may be sufficient to confirm accurate placement. In other applications, such as when applying a local anesthetic to block a nerve, knowledge of δ may be useful in locating the target, or the health professional may again rely on tissue changes in the ultrasonic image. On the ultrasound screen, indirect or secondary signs of needle location may include soft tissue deformation indicating that the needle is passing through that tissue, and a hypoechoic acoustic shadow and ring down artifact when the sound beam hits the needle. All of these secondary signs are important when the needle itself is not visualized. The crosshair (or another suitably chosen indicia) may provide a focus point to watch for the formation of these secondary signs. Since the needle pathway is shown on monitor 20, the health professional can focus his or her attention on the cross hair. Once the needle is located at the target by primarily visualizing the needle itself or by one of the secondary indicators above, a small portion of local anesthetic can be injected and may be detectable by the reflected sound waves so that a change in the ultrasonic image appears at the displayed cross hair. Likewise, once the needle tip is placed at the target by direct visualization or by secondary signs, the ultrasound guidance system can release the needle and then the transducer can be orientated in parallel with the needle insertion to visualize the entire length of the needle including the tip in relation to the target.

With reference to FIGS. 2, 3, 2A and 3A, accurate positioning of needle 50 with respect to its intended target 64 proceeds as follows. First, monitor 20 is positioned within the health professional's immediate field of view of the patient and ultrasound device, so as to avoid any occurrence of drift during the procedure. If, initially, monitor 20 displays a cross hair, e.g., cross hair 62a, above the target, then the needle pathway needs adjustment. This is done by rotating the angle of insertion of the needle 50 clockwise in FIG. 3A (of course, if cross hair 62a were located below target 64, then needle 50 would be rotated counterclockwise in FIG. 3A). This rotational motion is detected by a change in resistance in the potentiometer circuit. The processed signal produces real-time angular positional information for the needle pathway which is represented on monitor 20 as a downwardly moving cross-hair. As the needle pathway is adjusted downward by rotating needle 50, cross-hair 62a moves downward and towards target 64 until it reaches target 64, which corresponds to cross-hair 62b. Once the cross-hair is centered on the target, the desired needle pathway is located. It is desirable that, after the needle pathway is found, clip is able to stay in the corresponding position via a preset rotational resistance in shaft 43 of needle guidance portion 40. Preferably, the rotational resistance is provided to the shaft 43 by friction and a dampener coupled to shaft 43. Alternatively, the potentiometer assembly may provide the rotational resistance to shaft 43. Because the rotational resistance holds the needle in place without user assistance, the needle pathway can be reliably maintained. After needle pathway E is found, needle 50 can be inserted the distance $\delta(\theta_2)$ where target 64 is located. Once at target 64, probe 30 may be removed from needle 50. After probe 30 has been removed from needle 50, probe 30 may be set aside via the probe mounting hook 15 which is attached to monitor 20, as discussed earlier. Alternatively, probe 30 may be set aside onto the sterile field via the sterile shell 31 and an optional sterile sleeve that will extend down the length of the ultrasound cord 18. This maintains probe and cord sterility in the event that probe 30 is needed again. The remainder of the procedure may be performed in usual sterile fashion.

Assembly of probe 30 includes calibration of the needle guidance portion 40. That is, calibration of the changes in the potentiometer circuit with respect to changes in the needle angle and calibration of the angle data with depth positions on the ultrasonic image, e.g., cross-hair locations relative to the image plane displayed on monitor 20. It will be appreciated that the potentiometer (or position encoder) may be calibrated using any known method. After the angle data has been calibrated with respect to changes in the potentiometer circuit, incremental angular rotations of the needle may be determined from incremental changes in the potentiometer circuit using any well known interpolation algorithm. Depth position data, e.g., X, Y Offset Parameters of FIG. 5B, are then computed. These depth position data include the offset position of the needle pathway relative to the potentiometer and the position of the potentiometer relative to the transducer. These parameters are then used with the computed angular changes to compute the depth positions, i.e., the intersection of the needle pathway on the image plane.

As mentioned earlier, a needle guidance portion 40 is arranged so that angular positions of the needle are measured about an axis that lies in a plane parallel to a scanning plane B. Hence, probe 30 is configured for selectively positioning a needle in a plane transverse to scanning plane B. In other embodiments, angular positions of the needle are measured about any axis that lies in a plane perpendicular to a body surface to be penetrated by a needle received in the guidance portion, but not a plane that is parallel to the scanning plane. For example, angular positions may be measured with respect to a rotation axis that lies in a plane that makes at least a 10, 15, 30, 45, 60, 75, between 45 and 90 degrees, or up to 90 degree angle with the scanning plane. In these embodiments, the needle guidance portion may be constructed in a similar manner to needle guidance portion 40, but with its mounting to the transducer being such that the shaft about which the needle rotates is orientated so that the needle rotates in a plane perpendicular to a body surface to be penetrated by the needle but not a plane that is parallel to the scanning plane. Such embodiments can still offer the various advantages of the earlier disclosed embodiments, such as tracking a needle position relative to a target and aligning the needle with a target.

As mentioned, probe 30 is preferably encased in a sterile, disposable shell 31. Shell 31 is configured with a housing 34 that receives needle guidance portion 40, which is fit to an external portion of the transducer and encases the entire transducer. When fitting shell 31 to the transducer and needle guidance portion 40, a front and rear shell portion may be used in which the front and rear shell portions are brought together and held together by, e.g., snap fasteners.

Figure 6:
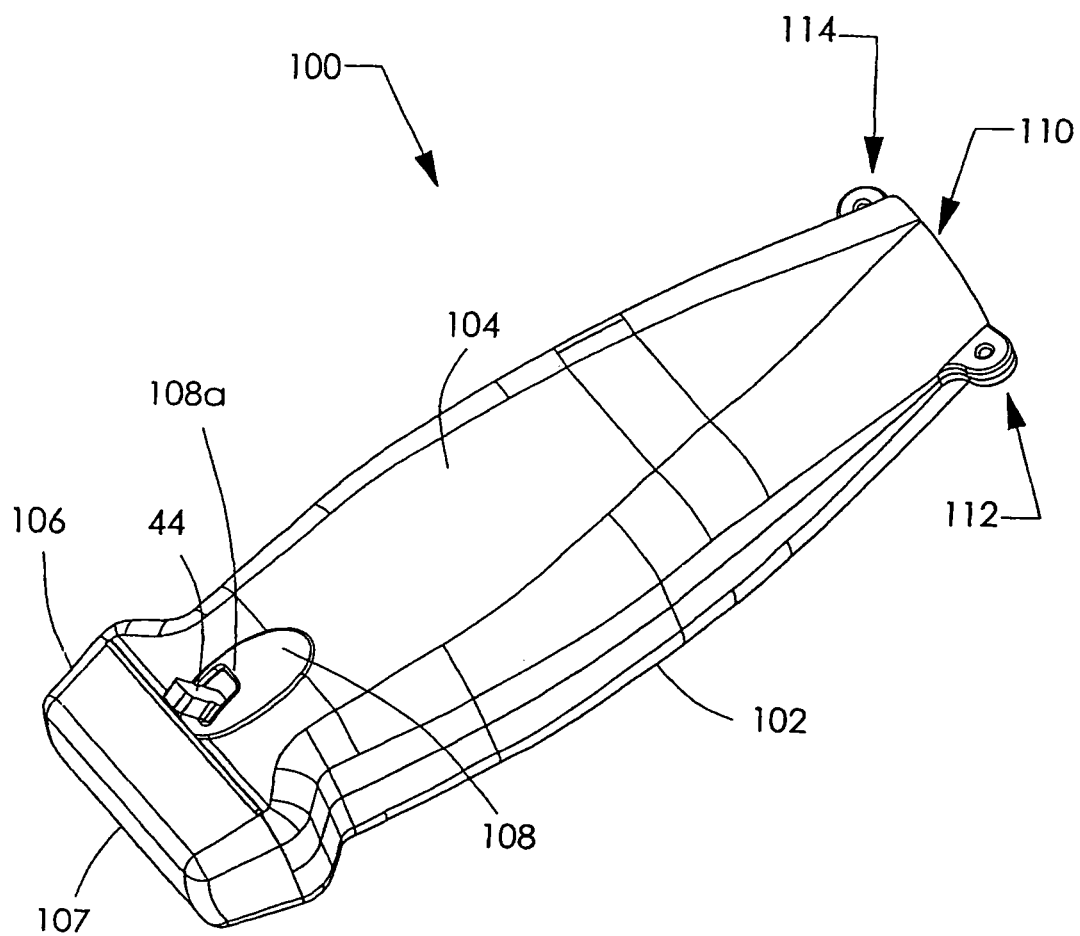
FIG. 6 is a perspective view of a second embodiment of an ultrasonic probe enclosed in a sterile shell.
Figure 7:
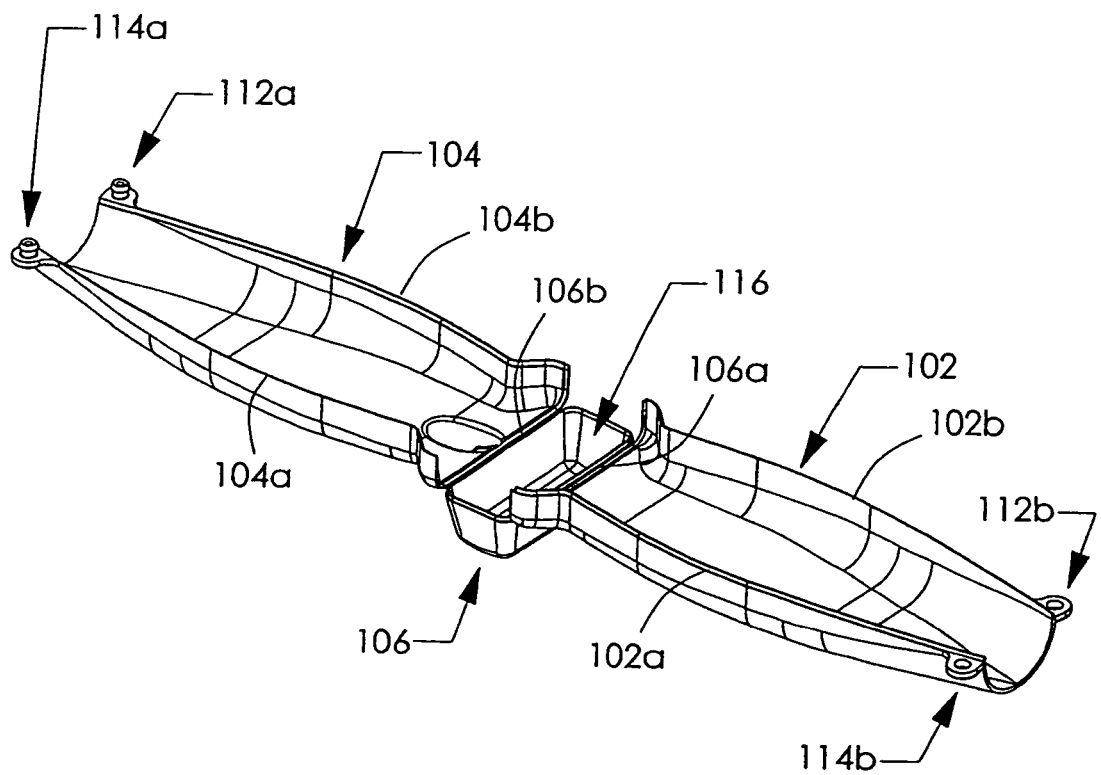
FIG. 7 is a perspective view of a sterile shell of the probe of FIG. 6.

A second embodiment of a sterile shell is illustrated in FIGS. 6 and 7. Shell 100, like shell 31 of the first embodiment, is a clamshell formed to cover the entire probe. However, shell 100 is formed to cover an embodiment of the ultrasonic probe where the needle guidance portion is integrated into the transducer body. Thus, in this embodiment, there is no need to provide a housing portion shaped for receiving needle guidance portion 40 as these components are provided with the transducer body. Shells 31 and 100 are preferably formed by injection molding, made of relatively rigid plastic, which is easily sealable, less prone to rips or tears than a conventional sleeve, and has an optional sleeve for procedures that require a sterile cord.

With reference to FIG. 6, shell 100 includes an upper portion 104, a lower portion 102 and a forward portion 106 encasing probe 30. A forward surface 107 of forward end 106 allows acoustic waves to pass through without appreciable attenuation. A rear end 110, formed by portions 102 and 104, provides an opening for a cord connecting probe 30 to monitor 20. A raised region 108 includes a slotted hole 108a sized to allow clip connector 44 to move freely within a predetermined range of angles for purposes of adjusting the angular orientation of a needle mounted to the probe, as discussed earlier. In an alternative embodiment, clip connector 44 may be disposed so as to be recessed within, or flush with hole 108a so as to maintain sterility. Additionally, needle clip 200 (receivable on clip connector 44) may be provided with a skirt near the end of post 224 so as to cover hole 108a for purposes of maintaining sterility, but without obstructing rotation of needle clip 200, as discussed earlier.

A pair of snap connectors 112, 114 or other suitable fasteners are used to hold upper and lower portions 102, 104 together. FIG. 7 illustrates shell 100 before enclosing the probe within. Shell 100 is a one-piece construction. Forward portion 106 is connected to upper portions 104 and lower portions 102 by living hinges 106a and 106b. The design of shell 100 is such that forward end 106 may be used as a container for acoustic coupling gel. Hence, shell 100 may be provided with acoustic gel in container area 116 and sealed by a removable lidstock.

The probe may be encased within shell 100 as follows. First, a lidstock sealing the acoustic gel is pealed off. This exposes the acoustic gel and allows the transmitting end of the probe to be inserted into space 116. Next, portions 102 and 104 are brought together by rotation about living hinges 106a, 106b until edges 102b, 102a, 104a and 104b mate together to form a sterile barrier. In order to facilitate a good sterile barrier, cooperating lap joints are formed on edges 102b, 102a, 104a and 104b. Male portions 112a, 114a and female portions 112b, 114b of snap connectors 112, 114 are then joined together by a snap fit. A protrusion is formed on the male portions 112a, 114a so that when it is time to remove the probe from shell 100, snap connectors 112, 114 may be disengaged by pressing down on male portions 112a, 114a.

As discussed above and described in greater detail, below, a disposable needle clip is used to secure a needle to the probe, e.g., probe 30 and this needle clip is attached to probe 30 at clip connector 44 after probe 30 is enclosed in shell 100. Needle clip 200, like shells 31 and 100, is sterile and stored sterilely until use. Therefore, potential contamination is minimized when snapping the shell onto the probe. The issue of maintaining sterility may be addressed by two features. First, clip connector 44 may be disposed so as to not extend beyond opening 35 or 108a of the completely closed shells 31 and 100. This prevents contamination of the shell opening by the non-sterile clip connector. Second, needle clip 200 may have a skirt that covers but does not touch the opening of hole 35 or 108a. This provides a second barrier and a tortuous path to prevent potential contamination of the sterile shell. Ideally, a needle clip and sterile shell are made available in pre-manufactured sterile kits each containing a sterile gel packet, a shell, at least one needle clip, and an optional sterile sleeve for the cord. Thus, there is provided a sterile external surface around the ultrasound probe and cord while allowing a needle clip and clip connector to rotate and be monitored by a potentiometer assembly.

Needle clip will now be described in greater detail with reference to probe 30. Needle clip is preferably designed so that the health professional may easily engage and disengage the needle clip as well as secure and release, respectively, a needle from probe 30 during the procedure. In particular, it is desirable that the needle clip be designed so that probe 30 may be disengaged from needle 50 so as to minimize any movement of the needle shaft while it is embedded within the patient. First, second, third and fourth embodiments of a needle clip will now be described with reference to FIGS. 8-11.

With reference to FIGS. 8A, 8B and 8C, a first embodiment of a needle clip 200 includes a first part 201 (FIG. 8A) and a second part 202 (FIG. 8B). In another embodiment, parts 201 and 202 may be a unitary, as opposed to a two-piece construction. A semi-circular cradle 204 for receiving the shaft of a needle is formed on second part 202. Second part 202 is sized for sliding engagement within a holding portion 226 of first part 200. When inserted in holding portion 226, ridges 212a, 212b engage with channels 228a, 228b, respectively, which are formed on side walls 226a, 226b of holding portion 226. A wall portion 208 of second part 202 has a surface 210 for abutment against surface 226c of holding portion 226 when second part 202 is completely received in holding portion 226. This contact between wall surface 210 and surface 226c ensures that second part 202 will stay in holding portion 226. Flexible fingers may be formed at an end of second part 202 for providing a positive connection between first part 201 and second part 202. The assembled needle clip 200 is secured to clip connector 44 by placing a hollow post 224 formed on first part 200 over clip connector 44. FIG. 8C illustrates the assembled needle clip 200 secured to clip connector 44 of probe 30.

Referring to FIGS. 8A and 8C, first part 201 includes a fastening arm 216 secured to post 224 by a flex member 222. At a first end 216a of fastening arm 216 a finger rest 220 is provided and at an opposite end a cover 216b is disposed adjacent to the holding portion 226. Flex member 222 has a curved shape which allows it to be easily bent towards holding portion 224 by finger pressure applied at finger rest 220. Clip connector 200 retains a needle in cradle 204 by applying constant finger pressure at finger rest 220. When finger pressure is applied to finger rest 220 (represented by force F in FIG. 8C), flex member 222 bends towards holding portion 226, which causes cover 216b to extend over cradle 204 (direction $d_1$ in FIG. 8C), thereby trapping the needle shaft between cover 216b and cradle 204. When it is time to separate the needle from the probe 30, the user simply removes the finger pressure applied to finger rest 220, which causes flex member 22 to return to its undeformed position, FIG. 8C, and cover 216b to move back to its initial position. By this action, the needle shaft can be separated from probe 30 without any extra movements, without the help of another health professional, without disengaging any mechanical connection and hence with minimal or no disruption to the needle shaft while it is embedded in the patient.

Figure 9:
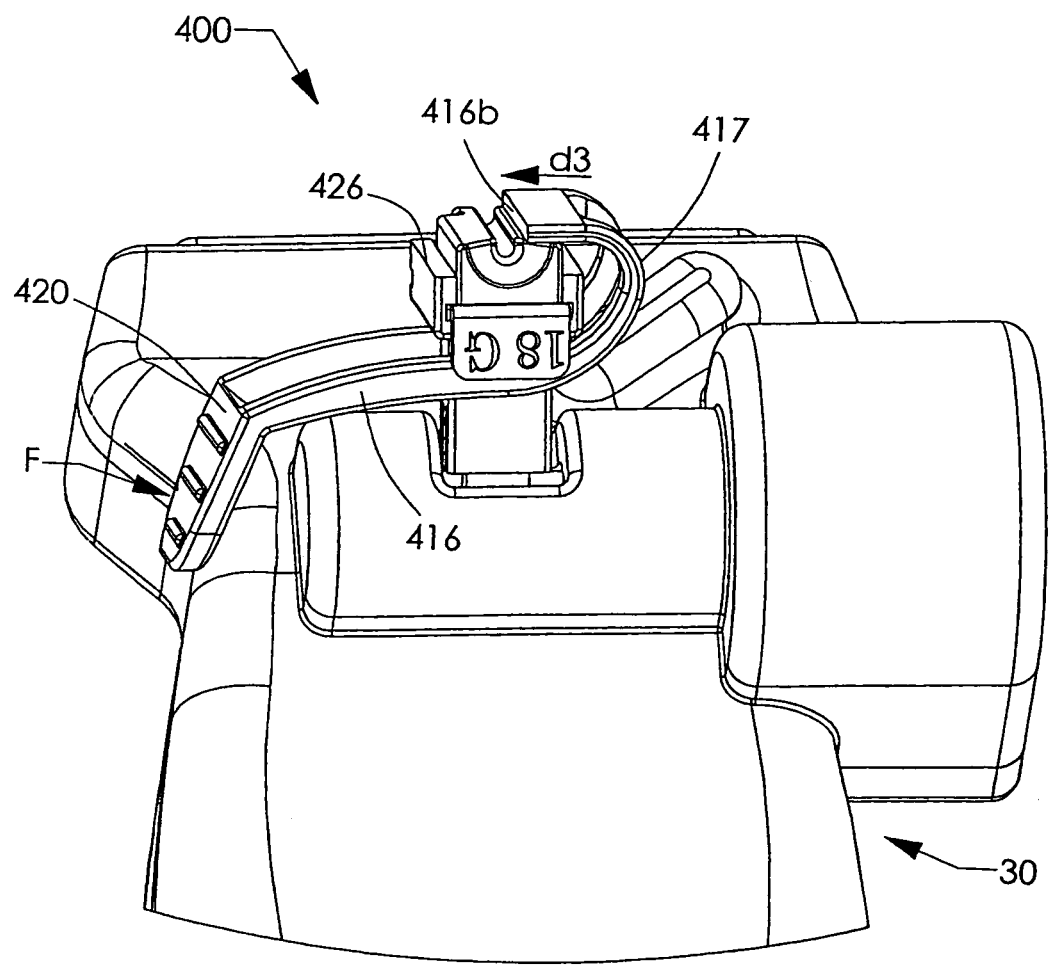
FIG. 9 is a perspective view of a second embodiment of a needle clip attached to the probe of FIG. 5 according to an embodiment of the present invention.

Second and third embodiments of a needle clip will now be described with reference to FIGS. 9 and 10. In the second embodiment, there is a first part and a second part to the needle clip, which can be secured to the clip connector 44 in the same fashion as needle clip 200. In the third embodiment, there are three parts to the needle clip. The same structure associated with the holding portion, post and second part as described above for needle part 200 is used in these other embodiments (alternatively, a one-piece and two-piece construction may be chosen over a two-piece and three-piece construction for these embodiments, respectively). However, these other embodiments differ in the structure and method of actuation associated with the fastening arm. Accordingly, discussion of the second and third embodiments will proceed with the understanding that the structure and functionality of the remaining structure associated with the needle clip will be readily understood in view of the discussion of the first embodiment.

A second embodiment of a needle clip 400 will now be described with reference to FIG. 9. In this embodiment, fastening arm 416 (attached to post 226 at front and back sides thereof) has a curved portion 417 that extends around holding portion 426 so that cover 416b is disposed adjacent to, and on the opposite side of cradle 204. Cover 416b extends over cradle 204 when finger pressure is applied, as in the first embodiment. Actuation of cover 416b is accomplished by pressing downward on finger rest 420, which causes cover 416b to move over cradle 204 (direction $d_3$) so that the needle shaft becomes trapped between cradle 204 and cover 416b. Needle may be removed form cradle 204 by releasing finger pressure so that cover 416b displaces back to its starting position (FIG. 9).

A third embodiment of a needle clip 500 will now be described with reference to FIG. 10. In this embodiment, a fastening arm 516 is slidingly received in a grooved section 522 of first part 201 that is disposed adjacent to cradle 204. A flex member 524 is attached to fastening arm 516 at a lower surface 516a and is adapted to abut a surface 524a of probe 30, which causes flex member 524 to flex towards finger rest 520 when finger pressure is applied at finger rest 520. Before finger pressure is applied, cover 516b does not cover cradle 204. When finger pressure is applied, cover 516b extends over cradle 204, thereby trapping needle shaft between cradle 204 and cover 516b. While finger pressure is applied, flex member 524 is maintained in a flexed state. When finger pressure is removed, flex member 524 will move cover 516b back to its original position (i.e., not covering cradle 204) as it returns to its undeformed state. Needle shaft may then be separated from probe 30. This embodiment, like the others described, can be used to separate needle shaft from probe 30 without disengaging any mechanical connection and hence with minimal disruption to the needle shaft while it is embedded in the patient.

Certain modifications and improvements will occur to those skilled in the art upon a reading of the foregoing description. By way of example, the sterile shell can be made to work with any existing ultrasound probe, providing a more convenient and operable sterile covering than traditional probe sleeves. Also, the cart-based compact ultrasound system can be modified to work with other types of available probes, providing a more complete and user friendly portable ultrasound system. Further, the present invention can be configured to work with three-dimensional and four-dimensional (real-time three-dimensional) ultrasound in addition to the above described embodiment using real-time two-dimensional ultrasound. All modifications and improvements have been omitted herein for the sake of conciseness and readability but are properly within the scope of the present invention.

What we claim is:

1. An ultrasonic probe comprising:
   a transducer adapted for generating ultrasonic images of a scanning plane;
   a shaft operably coupled to the transducer, the shaft rotatable about an axis parallel to the scanning plane;
   a position detector coupled to the shaft; and
   a needle holder connected to the shaft and extending outwardly therefrom, the needle holder rotatable with the shaft, the needle holder comprising a needle holding portion configured to receive the shaft of a needle and providing an anticipated needle path corresponding to the shaft of the needle, the anticipated needle path being opposed to the scanning plane.

* * * * *